(12) United States Patent
Tsai (10) Patent No.: US 6,855,138 B2
(45) Date of Patent: Feb. 15, 2005

(54) INJECTION JOINT FOR AN INTRAVENOUS (IV) DEVICE TUBE

(75) Inventor: Hsi-Chin Tsai, 2F, No. 524, Ta-An Rd., Shulin City, Taipe Hsien (TW)

(73) Assignees: Hsi-Chin Tsai, Taipei Hsien (TW); Wen-Neng Liu, Taipei (TW)

( * ) Notice: Subject to any disclaimer, the term of this patent is extended or adjusted under 35 U.S.C. 154(b) by 62 days.

(21) Appl. No.: 10/615,207

(22) Filed: Jul. 8, 2003

(65) Prior Publication Data

US 2005/0010177 A1 Jan. 13, 2005

(51) Int. Cl.[7] ............................................. A61M 25/16
(52) U.S. Cl. ...................... 604/537; 604/538; 604/539
(58) Field of Search ................................ 604/246, 247, 604/256, 523, 533–539

(56) References Cited

U.S. PATENT DOCUMENTS

| | | | | |
|---|---|---|---|---|
| 4,752,292 A | * | 6/1988 | Lopez et al. ................ | 604/244 |
| 4,909,798 A | * | 3/1990 | Fleischhacker et al. ..... | 604/256 |
| 4,981,469 A | * | 1/1991 | Whitehouse et al. ......... | 604/86 |
| 5,108,380 A | * | 4/1992 | Herlitze et al. ............. | 604/533 |
| 5,456,675 A | * | 10/1995 | Wolbring et al. ........... | 604/537 |
| 5,603,706 A | * | 2/1997 | Wyatt et al. ................ | 604/539 |
| 5,782,816 A | * | 7/1998 | Werschmidt et al. ....... | 604/256 |
| 6,325,782 B1 | * | 12/2001 | Lopez ......................... | 604/249 |
| 2002/0147431 A1 | * | 10/2002 | Lopez et al. ................ | 604/256 |

* cited by examiner

*Primary Examiner*—Sharon Kennedy
(74) *Attorney, Agent, or Firm*—William E. Pelton, Esq.

(57) ABSTRACT

An injection joint for an IV device tube has a connector with a sealed injection port. The sealed injection port has an injection port socket, a resilient plug and a cap. The resilient plug is mounted in the injection port socket and has a tapered flange and multiple through holes. The cap has a threaded nipple and is securely mounted in the injection port socket around the resilient plug. The tapered flange selectively blocks the threaded nipple. When adding medicinal solution to the injection joint, a syringe without a needle but with an inner threaded opening is screwed onto the threaded nipple of the cap. Pushing the tapered flange into an axial passage in the neck allows the medicinal solution to pass through the through holes and into the injection port socket. The present invention improves the safety to medical personnel when injecting solution into the injection joint.

7 Claims, 8 Drawing Sheets

INJECTION JOINT FOR AN INTRAVENOUS (IV) DEVICE TUBE

BACKGROUND OF THE INVENTION

1. Field of the Invention

The present invention relates to an injection joint, and more particularly to an injection joint for a intravenous (IV) device tube to allow a medicinal solution to be added to an IV drip without using a needle without interrupting the IV drip.

2. Description of Related Art

Since some patients cannot ingest nutrients or medicine orally, nutrients or medicine must be administered in an intravenous (IV) dripcontainer.

Figure 8:
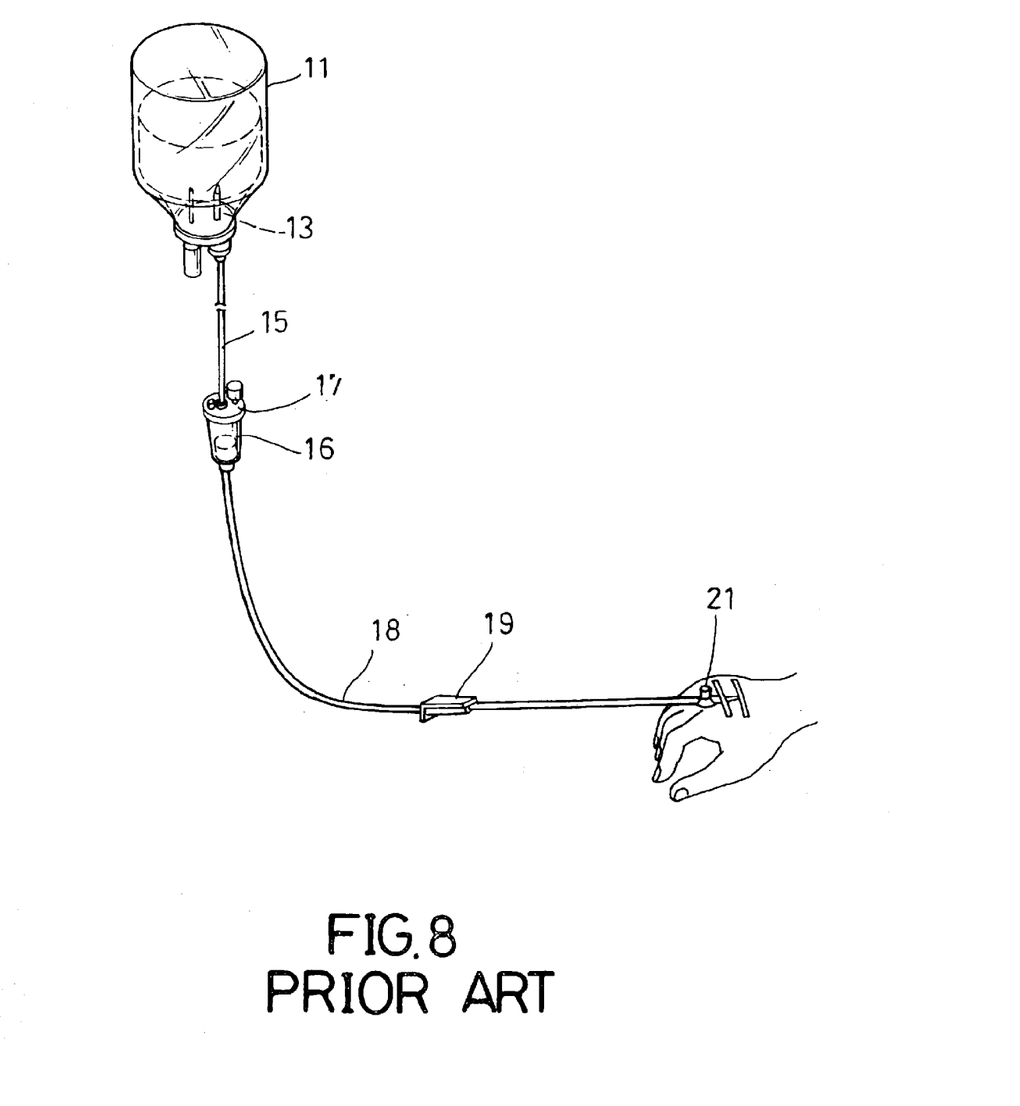
FIG. 8 is a perspective view of a conventional IV device in accordance with the prior art.

With reference to FIG. 8, a conventional IV solution container (11) must have an IV tube assembly (not numbered) to connect the IV solution container (11) to a patient (not numbered). The IV tube assembly also controls how quickly the IV solution is administered and provides a means to inject medicine into the IV solution. The IV tube assembly comprises a container needle (13), an upper IV tube (15), a lower IV tube (18), an injection joint (not numbered), a flow control apparatus (19) and a hypodermic needle (21).

The upper IV tube (15) has an upper end (not numbered) and a lower end (not numbered).

The container needle (13) is eccentric cavity, is connected to the upper end of the upper IV tube (15) and is inserted into the IV solution container (11).

One embodiment of the conventional injection joint comprises an intermediate container (16) and a lid (17). The intermediate container (16) has a bottom) (not numbered), an open top (not shown) and a discharge outlet (not numbered). The discharge outlet is formed on the bottom of the intermediate container (16) and is connected to the upper end of the lower IV tube (18). The lid (17) has a top (not numbered), an inlet (not numbered) and at least one sealed injection port (not numbered) and is mounted securely on the open top of the intermediate container (16). The inlet is formed through the top of the lid (17), and the lower end of the upper IV tube (15) is connected to the inlet. The at least one sealed injection port is tubular and has an internal passage (not shown) and an internal resilient seal (not shown). The internal passage passes through the lid (17) so a hypodermic needle (not shown) on a syringe (not shown) can puncture the resilient seal and inject medicine into the intermediate container (16).

The flow control apparatus (19) is mounted around the lower IV tube (18) to control how quickly IV solution flows to a patient.

The hypodermic needle (21) is connected to the lower end of the lower IV tube and is inserted in a patient's vein so the IV solution can be administered to a patient.

Figure 9:
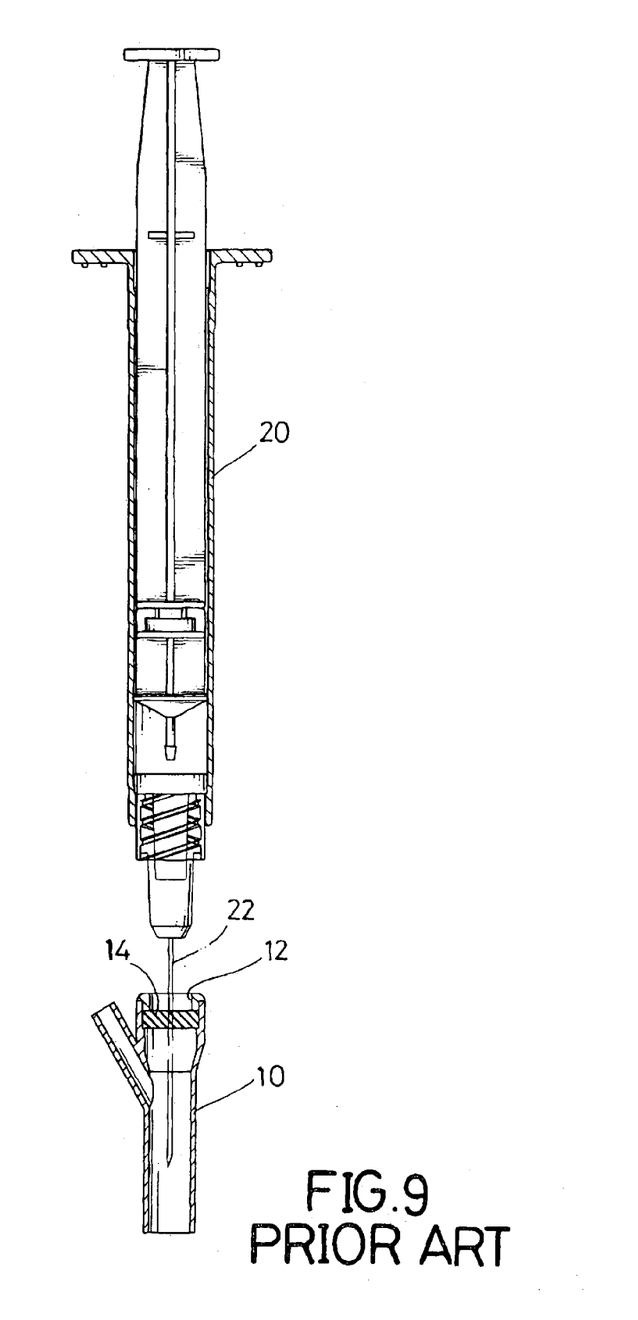
FIG. 9 is an operation perspective view of a second embodiment of a conventional injection joint for an IV tube in accordance with the prior art when a syringe with a needle injects liquid medication into the injection joint.

With reference to FIG. 9, another conventional injection joint is a Y-shaped tubular connector (10) and has an inlet (not numbered), a sealed injection port (12) and an outlet (not numbered). The inlet is connected to an IV solution container (not shown) through an upper IV tube (not shown), and the outlet is connected to a hypodermic needle (not shown) through a lower IV tube (not shown). The sealed injection port (12) is sealed with an internal resilient plug (14).

Since some patients need intravenous medication in addition to an IV solution, medication can be injected into the IV solution through the sealed injection port (12). A syringe (20) with a needle (22) is used to inject the medication by puncturing the resilient plug (14) with the needle (22). The medication in the syringe (20) is injected into the sealed injection port (12).

However, use of a syringe (20) with a needle (22) inherently subjects medical personnel to the possibility of injury. A contaminated needle (22) can transfer diseases to a people stabbed with the contaminated needle (22). Not using a needle (22) will improve the safety to medical personnel when injecting medication into the sealed injection port (12).

SUMMARY OF THE INVENTION

The main objective of the present invention is to provide an injection joint for an IV device tube to add medication to an IV solution without using a needle.

To achieve the objective, an injection joint for an IV device tube in accordance with the present invention comprises a connector with a sealed injection port. The sealed injection port has an injection port socket, a resilient plug and a cap. The resilient plug is mounted in the injection port socket and has a tapered flange and multiple through holes. The cap has an threaded nipple and is securely mounted in the injection port socket and around the resilient plug. The tapered flange of the resilient plug blocks the threaded nipple. When adding a liquid medication to the injection joint, a syringe without a needle has an inner threaded opening is screwed onto the threaded nipple of the cap. Pressure applied to the liquid medication by the syringe pushes the tapered flange into the cap and the liquid medication passes through the through holes, into the injection port socket and mixes with the IV solution. The present invention improves the safety when injecting a liquid medication into the injection joint.

Further benefits and advantages of the present invention will become apparent after a careful reading of the detailed description with appropriate reference to the accompanying drawings.

DETAILED DESCRIPTION OF THE INVENTION

An injection joint for an intravenous (IV) device tube in accordance with the present invention comprises a connector with a first internal passage, an inlet, an outlet and a sealed injection port. The inlet is connected to an IV container through an upper IV tube and communicates with the first internal passage in the injection joint. The outlet is connected to a hypodermic needle through a lower IV tube and communicates with the first internal passage of the injection joint.

With reference to FIGS. 1, 2, 6 and 7, the sealed injection port comprises an injection port socket (31), a resilient plug (40) and a cap (50). The injection port socket (31) is formed on the connector (30, 30a, 30b) and has a proximal end (not numbered), a distal end (not numbered), a bottom plane (34), a sidewall (not numbered), a protrusion (35) and an annular groove (33). The bottom plane (34) has a center (not numbered). The protrusion (35) has a top (not numbered) and a second internal passage (32) is formed integrally with and extends from the center of the bottom plane (34) of the injection port socket (31) and may be tapered. The second internal passage (32) communicates with the first internal passage in the connector (30, 30a, 30b). The sidewall has an inner face (not numbered) with a bottom (not numbered). The annular groove (33) is formed around the bottom of the inner face of the sidewall.

Figure 3:
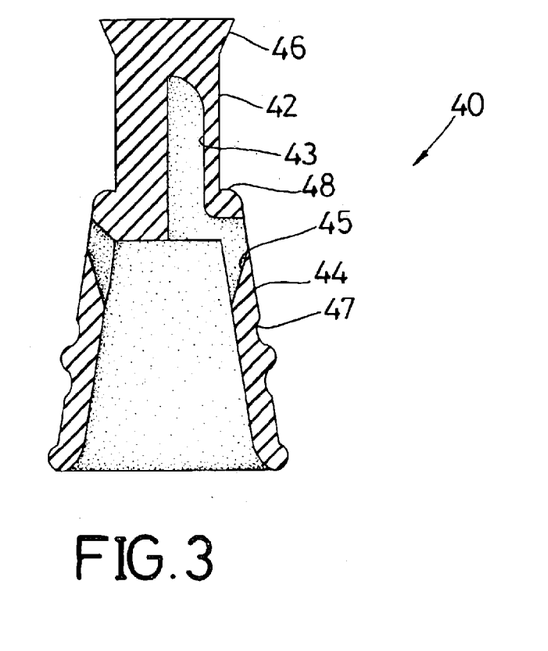
FIG. 3 is a cross sectional side plan view of a resilient plug in the injection joint in FIG. 1.
Figure 4:
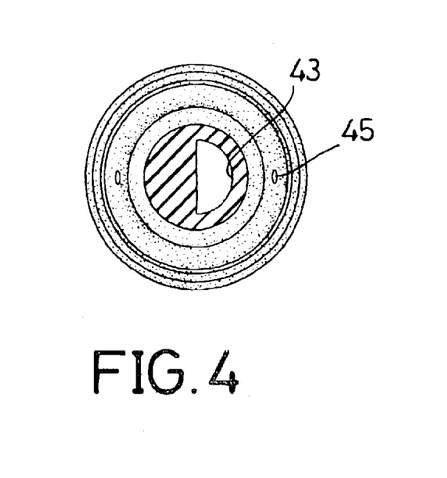
FIG. 4 is a cross sectional top plan view of the resilient plug along line 4—4 in FIG. 3.

With further reference to FIGS. 3 and 4, the resilient plug (40) has a neck (42), a bottom tube (44), an eccentric cavity (43), a tapered flange (46) and an annular shoulder (48). The neck (42) is cylindrical and has a top (not numbered) and a bottom (not numbered), and the eccentric cavity (43) is formed inside the neck (42). The eccentric cavity (43) may be formed in about half of the neck (42). The tapered flange (46) is formed integrally with and extends upward and tapers out from the top of the neck (42). The bottom tube (44) is formed integrally with and extends downward from the bottom of the neck (42) and has at least one annular constriction (47) and multiple through holes (45). The bottom tube (44) is larger than the neck (42) and the annular shoulder (48) is formed where the bottom tube (44) joins the neck (42). The annular constriction (47) is formed around the bottom tube (44). Multiple through holes (45) are formed near the annular shoulder (48) and passed through the bottom tube (44). The bottom tube (44) may taper out toward the bottom to fit over the protrusion (35) in the injection port socket (31). The bottom tube (44) is mounted on the protrusion (35) in the injection port socket (31).

The cap (50) has a distal end (not numbered), a proximal end (not numbered), a threaded nipple (52) and a mounting ring (56). The threaded nipple (52) is formed integrally with and extends upward from the distal end of the cap (50), has an internal surface (not numbered), a top end (not numbered), a bottom (not numbered) a tapered opening (54) and an axial passage (not numbered). The tapered opening (54) is formed in the top end of the threaded nipple (52) and communicates with the axial passage. The tapered opening (54) corresponds to the tapered flange (46) on the resilient plug (40). The neck (42) of the resilient plug (40) is mounted in the axial passage in the threaded nipple (52), and the tapered flange (46) on the resilient plug (40) closes the tapered opening (54) in the threaded nipple (52). The annular shoulder (48) of the resilient plug (40) abuts the bottom of the threaded nipple (52). The mounting ring (56) is formed integrally with and extends downward from the proximal end of the cap (50) and has an annular lip (58). The mounting ring (56) is mounted in the injection port socket (31). The annular lip (58) is formed integrally with and extends radially out from the mounting ring (56) and corresponds to the annular groove (33) in the injection port socket (31). The annular lip (58) is securely mounted in the annular groove (33) to securely hold the cap (50) in the injection port socket (31) and around the resilient plug (40).

Figure 1:
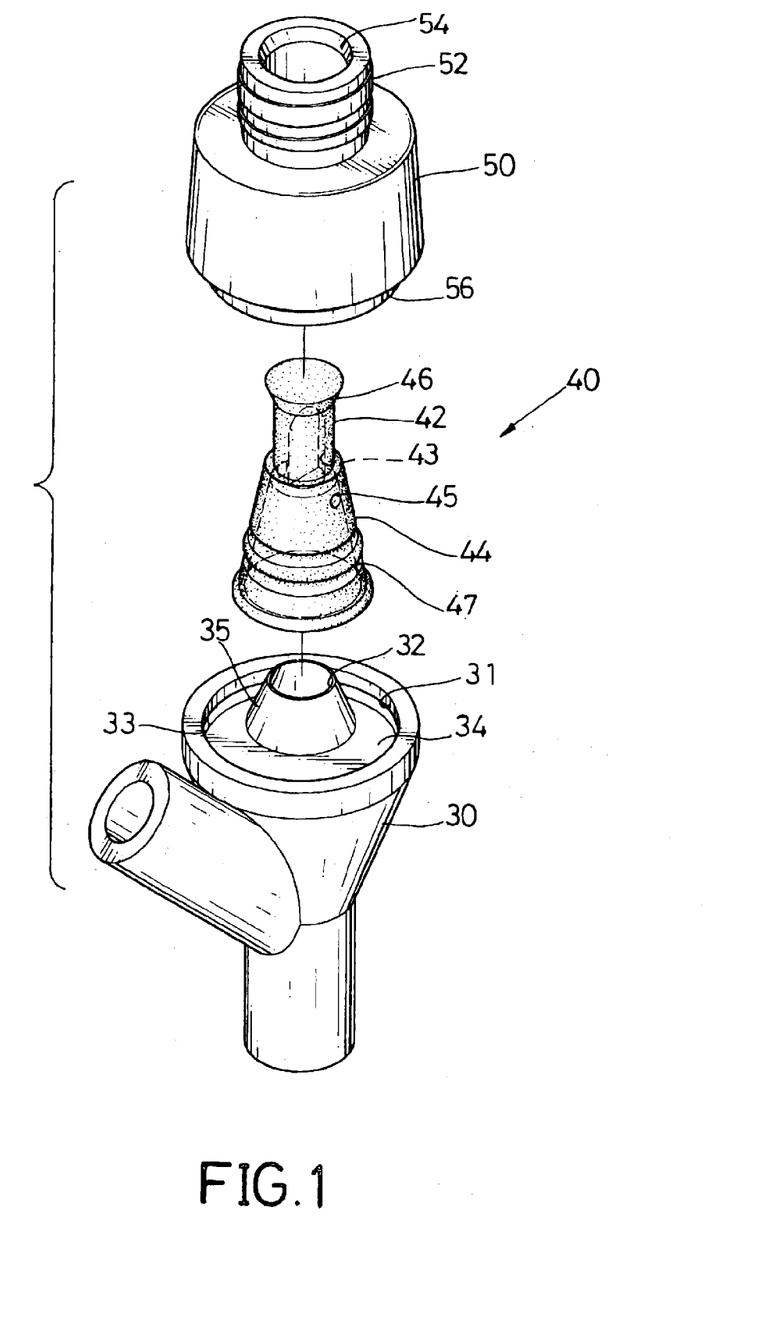
FIG. 1 is an exploded perspective view of a first embodiment of an injection joint for an IV device tube in accordance with the present invention.
Figure 2:
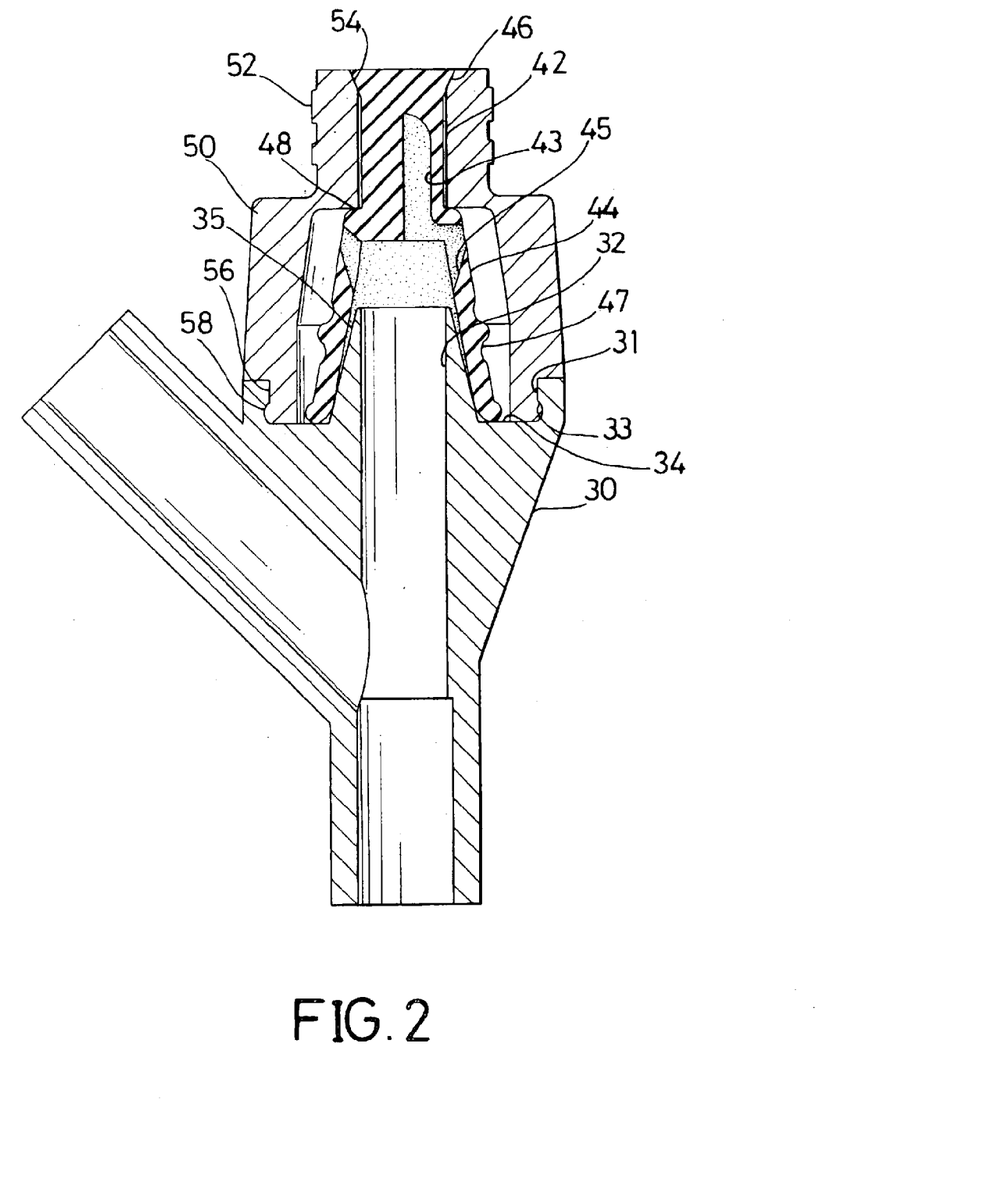
FIG. 2 is a cross sectional side plan view of the injection joint in FIG. 1.
Figure 6:
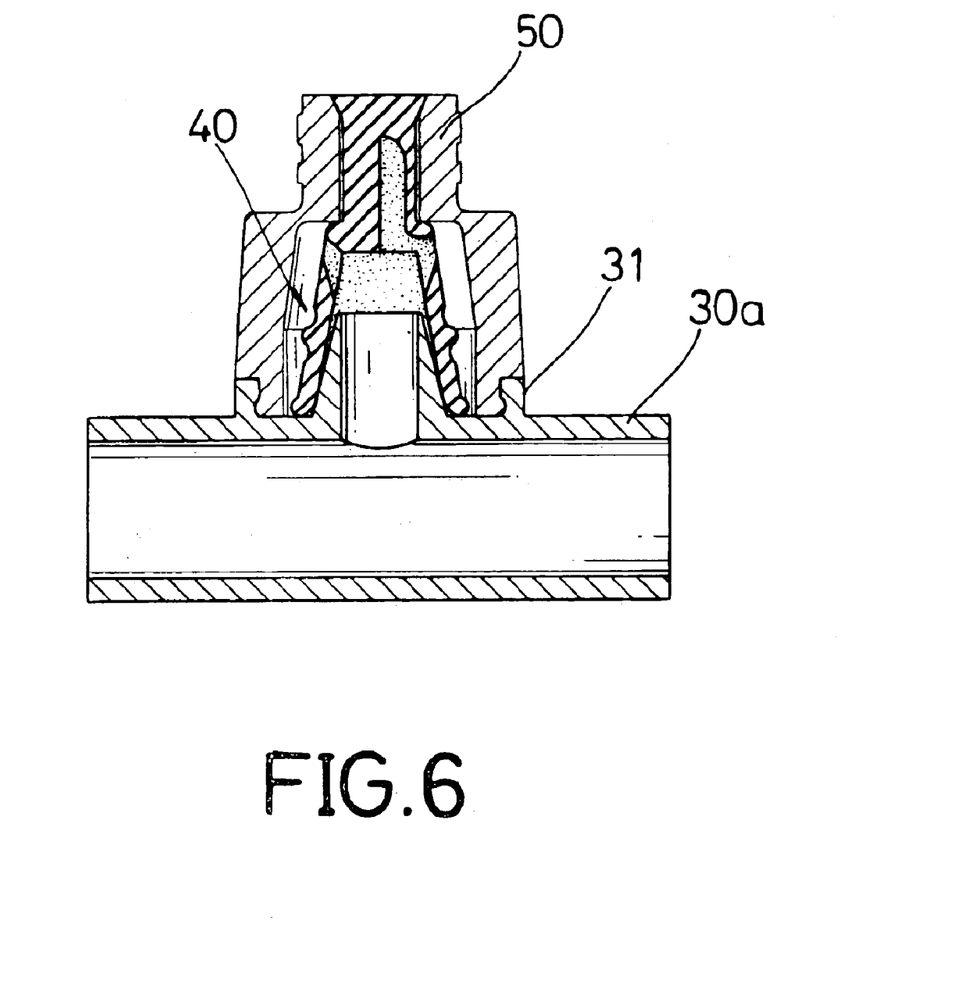
FIG. 6 is a cross sectional side plan view of a second embodiment of the injection joint for an IV device tube in accordance with the present invention.
Figure 7:
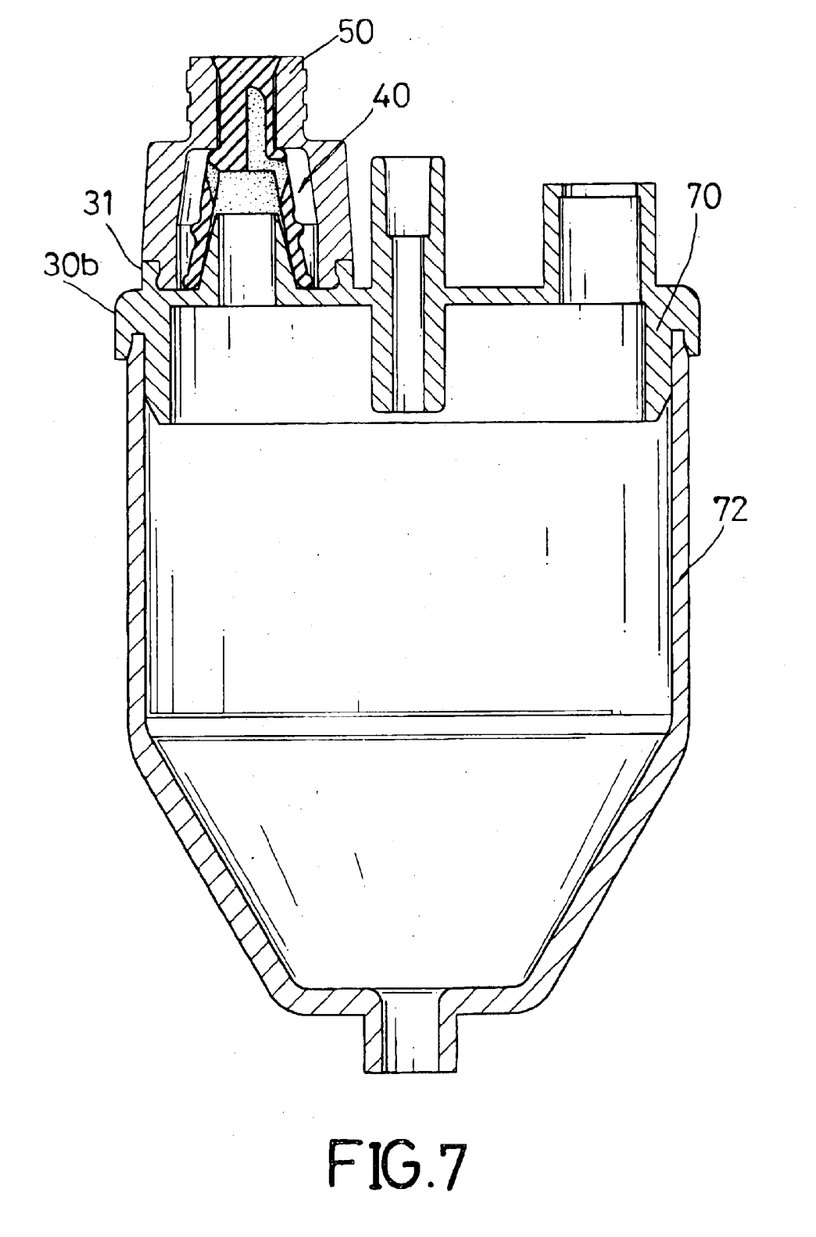
FIG. 7 is a cross sectional side plan view of a third embodiment of the injection joint for an IV device tube in accordance with the present invention.

With reference to FIGS. 1, 2 and 6, a first and a second embodiment of the connector (30, 30a) of the injection joint for the IV device tube in accordance with the present invention is a tubular connector (30, 30a). The first embodiment of the tubular connector (30) is Y-shape, and the second embodiment of the tubular connector (30a) is T-shaped. The tubular connectors (30, 30a) each has an inlet (not numbered), an outlet (not numbered), a first internal passage and an injection port. The inlet is connected to an IV container (not shown) through an upper IV tube (not shown) and communicates with the first internal passage. The outlet is connected to a hypodermic needle (not shown) through a lower IV tube (not shown) and communicates with the first internal passage. The injection port communicates with the second internal passage (32) in the injection port socket (31). With reference to FIG. 7, a third embodiment of the injection joint in accordance with the present invention has a connector (30b) with a different structure. The third embodiment of the connector (30b) has a lid (70) and an intermediate container (72). The intermediate container (72) has a top (not numbered), a bottom (not numbered), a wide upper opening (not numbered) and an outlet (not numbered). The lid (70) has an inlet (not numbered) and at least one sealed injection port (not numbered). The inlet is connected to an IV solution container (not shown) through an upper IV tube (not shown). The at least one sealed injection port is the same as previously described. The outlet is connected to a hypodermic needle (not shown) through a lower IV tube (not shown).

Figure 5:
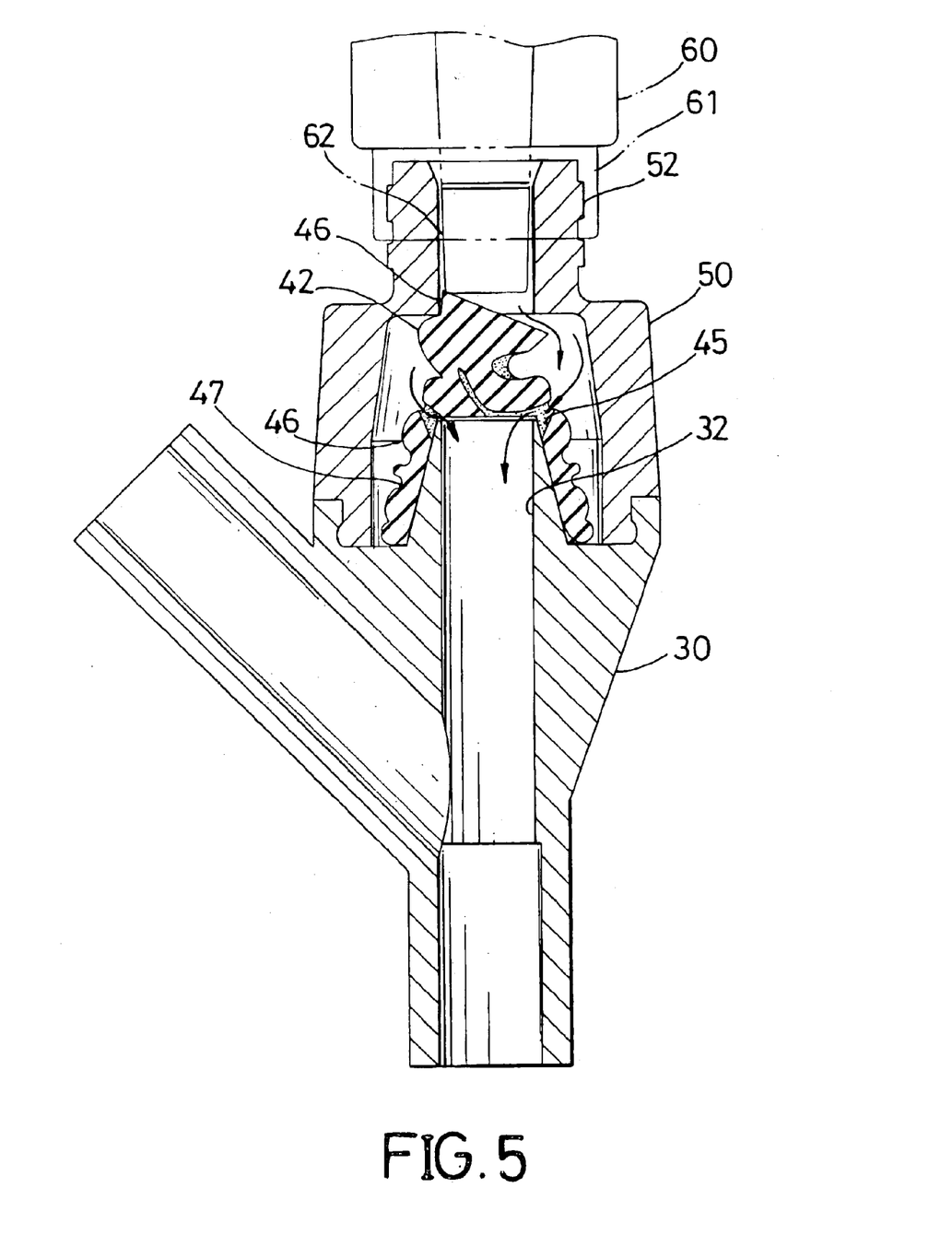
FIG. 5 is an operational cross sectional side plan view of the injection joint in FIG. 1 when liquid medication is injected into the injection joint.

With reference to FIG. 5, a syringe (60) without a needle and with an inner threaded opening (61) and a plunger (not numbered) with a head (62) slidably received in the syringe (60) is used to inject a medicinal solution into the injection joint. When adding a medicinal solution to an IV solution (not shown) through the injection joint, the inner threaded opening (61) is screwed onto the threaded nipple (52) of the cap (50). Pushing the plunger causes the head (62) on the plunger to push the tapered flange (46) of the resilient plug (40) into the axial passage in the threaded nipple (52). The pressure of the liquid medicine on the resilient plug (40), the annular constriction (47) in the bottom tube (44) and the eccentric cavity (43) in the neck (42) cause the neck (42) and tapered flange (46) of the resilient plug (40) to collapse and open the axial passage in the threaded nipple (52). The medicinal solution can pass through the through holes (45) in, the resilient plug (40) and the internal passage (32) in the injection port socket (31).

In the present invention, the tubular connector (30, 30a, 30b) does not use a needle to add a medicinal solution and improves the safety to the medical personnel.

Although the invention has been explained in relation to its preferred embodiment, it is to be understood that many other possible modifications and variations can be made without departing from the spirit and scope of the invention as hereinafter claimed.

What is claimed is:

1. An injection joint for an intravenous (IV) device tube and comprising
   a connector with a first internal passage, an inlet, an outlet and a sealed injection port, wherein the inlet communicates with the first internal passage, the outlet communicates with the first internal passage and the sealed injection port comprises an injection port socket formed on the connector and comprising
- a proximal end;
- a distal end;
- a sidewall having an inner face with a bottom;
- a bottom plane having a center;
- a protrusion having a top and a second internal passage and formed integrally with and extending from the center of the bottom plane of the injection port socket, wherein the second internal passage communicates with the first internal passage in the connector; and
- an annular groove formed around the bottom of the inner face of the sidewall;

a resilient plug attached to the injection port socket and comprising
- a cylindrical neck with a top end and a bottom;
- an eccentric cavity formed in the neck;
- a tapered flange integrally formed with and extending upward from the top end of the neck wherein the the tapered flange is larger than the neck; a bottom tube formed integrally with and extending downward from the bottom of the neck and mounted on the protrusion in the injection port socket, wherein the bottom tube is larger than the the neck and has
- an annular constriction formed around the bottom tube; and
- multiple through holes; and
- an annular shoulder formed where the neck joins the bottom tube; and a cap attached to the injection port socket, mounted around the resilient plug and comprising
- a distal end;
- a proximal end;
- a threaded nipple formed integrally with and extending upward from the distal end of the cap and having an axial passage, a top end and an opening formed in the top end, wherein the opening corresponds to the tapered flange of the resilient plug and the neck of the resilient plug is mounted in the axial passage in the threaded nipple and the tapered flange of the resilient plug is mounted in the opening in the threaded nipple when the resilient plug is mounted in the cap;
- a mounting ring formed integrally with and extending downward from the proximal end of the cap, wherein the mounting ring is mounted in the injection port socket; and
- a annular lip formed integrally with and extending radially out from the mounting ring, wherein the annular lip corresponds to and is securely held in the annular groove.

2. The injection joint for an intermediate device tube as claimed in claim 1, wherein the connector is tubular.

3. The injection joint for an intermediate device tube as claimed in claim 2, wherein the tubular connector is Y-shaped.

4. The injection joint for an intermediate device tube as claimed in claim 2, wherein the tubular connector is T-shaped.

5. The injection joint for an intermediate device tube as claimed in claim 1, wherein the connector has
an intermediate container having
- a top;
- a bottom;
- a wide upper opening at the top; and
- an outlet at the bottom and adapted to be connected to a hypodermic needle through a lower IV tube; and
- a lid mounted on the wide upper opening of the intermediate container and having an inlet adapted to be connected to an IV solution container through an upper IV tube.

6. The injection joint for an IV device tube as claimed in claim 1, wherein the protrusion of the injection port socket is tapered and the bottom tube of the resilient plug is tapered and corresponds to the protrusion in the injection port socket.

7. The injection joint for an IV device tube as claimed in claim 1, wherein the eccentric cavity is formed inside half of the neck.

* * * * *